United States Patent [19]

Gulliver

[11] Patent Number: 4,944,927

[45] Date of Patent: Jul. 31, 1990

[54] PROCESS FOR THE RECOVERY OF METALS

[75] Inventor: David J. Gulliver, North Humberside, England

[73] Assignee: BP Chemicals Limited, London, England

[21] Appl. No.: 355,850

[22] Filed: May 17, 1989

Related U.S. Application Data

[63] Continuation of Ser. No. 79,513, Jul. 30, 1987, abandoned.

[30] Foreign Application Priority Data

Jul. 31, 1986 [GB] United Kingdom ............... 8618710

[51] Int. Cl.$^5$ ............................................. C01G 55/00
[52] U.S. Cl. ............................. 423/22; 423/DIG. 14; 502/22; 502/28
[58] Field of Search .................... 423/22, DIG. 14; 502/22, 28; 75/101 R, 101 BE, 121

[56] References Cited

U.S. PATENT DOCUMENTS

| | | | |
|---|---|---|---|
| 4,364,907 | 12/1982 | Barnes | 423/22 |
| 4,388,217 | 6/1983 | Hembre et al. | 423/22 |
| 4,390,473 | 6/1983 | Cooper | 423/22 |
| 4,476,237 | 10/1984 | Porcelli | 502/28 |
| 4,578,368 | 3/1986 | Zoeller | 423/22 |

FOREIGN PATENT DOCUMENTS

| | | | |
|---|---|---|---|
| 879601 | 8/1971 | Canada | 423/22 |
| 1290535 | 1/1968 | Fed. Rep. of Germany | 423/22 |

Primary Examiner—Robert L. Stoll
Attorney, Agent, or Firm—Nixon & Vanderhye

[57] ABSTRACT

A process for recovering Group VIII metals from process streams derived from carbonylation processes is provided. The process comprises contacting the process stream with an extracting stream comprising acetic acid in water and thereafter recovering the extracting stream. The process stream is preferably one which contains tar and is produced by diluting a side stream from a carbonylation reactor with methyl iodide. During the process the Group VIII metal is extracted into the extracting stream from the process stream.

12 Claims, 2 Drawing Sheets

PROCESS FOR THE RECOVERY OF METALS

This is a continuation of application Ser. No. 079,513, filed 30 July 1987, now abandoned.

The present invention relates to the noble metal catalysts and optionally their associated promoters and copromoters from the products arising from carbonylation processes. More specifically the present invention relates to a process whereby Group VIII noble metal catalysts and their associated promoters and copromoters are recovered from products streams containing high boiling organic polymers (known in the art as tars) which have been produced as byproducts in such carbonylation processes.

Group VIII noble metal catalysed carbonylation processes are now well known in the art and are in some cases operated commercially. Typical examples of such processes include (a) the rhodium catalysed hydroformylation of olefins to higher alcohols, aldehydes and ketones; (b) the rhodium catalysed carbonylation of methanol to acetic acid; (c) the rhodium catalysed carbonylation of methyl acetate to acetic anhydride or ethylidene diacetate and (d) the rhodium catalysed carbonylation of methyl acetate, water and methanol to produce both acetic anhydride and acetic acid as described in European Patent No. 87870.

A problem often encountered with processes of this type is that, in addition to the desired products, there is often formed, as byproduct, considerable quantities of a high molecular weight organic polymer (tar). On commercial plants, where the high boiling materials and catalyst tend to be continually recycled, the formation of such tars is particularly undesirable since they tend to build up in the carbonylation reactor and eventually reduce the rats of carbonylation. To avoid build up of such tars, it is therefore necessary to remove continually a side stream from the catalyst recycle stream or the carbonylation reactor contents and treat it in a way such that the tars are separated from any Group VIII noble metal catalyst and any associated promoters and copromoters. The Group VIII noble metal catalyst and associated promoters and copromoters can then be returned directly or indirectly to the carbonylation reactor whilst the tars can be disposed of.

One approach to such a separation/recovery is to distil the side stream down to a solid residue comprising mainly Group VIII noble metal, promoters and copromoters and then treat the residue with a solubilising liquid, such as a strong acid. The Group VIII noble metal, promoters and copromoters dissolve in the solubilising liquid and can then be recovered from the solubilising liquid using standard techniques. Although such a process can in principle be used on a commercial plant it suffers from the disadvantage that it cannot easily be operated continuously.

An alternative process, which can be operated continuously, has been described in U.S. Pat. No. 4388217. The process, which is suitable for treating tars which arise during the production of acetic anhydride by the rhodium catalysed, iodide promoted, lithium copromoted reaction of methyl acetate with carbon monoxide, comprises contacting a reactor side stream containing tar, rhodium catalyst, iodide promoter and lithium copromoter, after dilution with methyl iodide, with aqueous hydroiodic acid in a countercurrent extractor. During the extraction, the rhodium, iodide and lithium migrate into the aqueous phase whilst the water immiscible tar and methyl iodide remain as a separate organic phase. The two phases are separated after the extraction by known methods and the tar disposed of after further separation from the methyl iodide. As regards the aqueous hydroiodic acid leaving the extractor this can be treated to recover the rhodium, iodide and lithium components which are then recycled to the carbonylation reactor.

Although the process described in U.S. Pat. No. 4388217 has the advantage that it is efficient and can be used to process continuously a side stream from the carbonylation reactor or product flash tank it has certain disadvantages. One disadvantage is that the aqueous hydroiodic acid stream is very corrosive and necessitates the use of special plant. A further disadvantage is the need to recover the rhodium, iodide and lithium components from the aqueous stream. Although it is taught that the aqueous hydroiodic acid containing rhodium, iodide and lithium values, can be recycled direct to the carbonylation reactor this is in practice not desirable since the presence of hydroiodic acid leads to a build up of methyl iodide in the main plant. As a consequence, it may be necessary to employ ancillary equipment to recover the methyl iodide and convert it back into hydroiodic acid or otherwise purge excess iodide from the plant.

A process has now been devised which allows Group VIII noble metals and any associated promoters and copromoters to be recovered from streams containing a tar without the disadvantages of employing aqueous hydroiodic acid as an extracting medium. The process is based on the surprising discovery that, contrary to the teaching of U.S. Pat. No. 4388217 efficient extraction can be achieved by employing aqueous acetic acid as the extracting medium.

Figure 1:
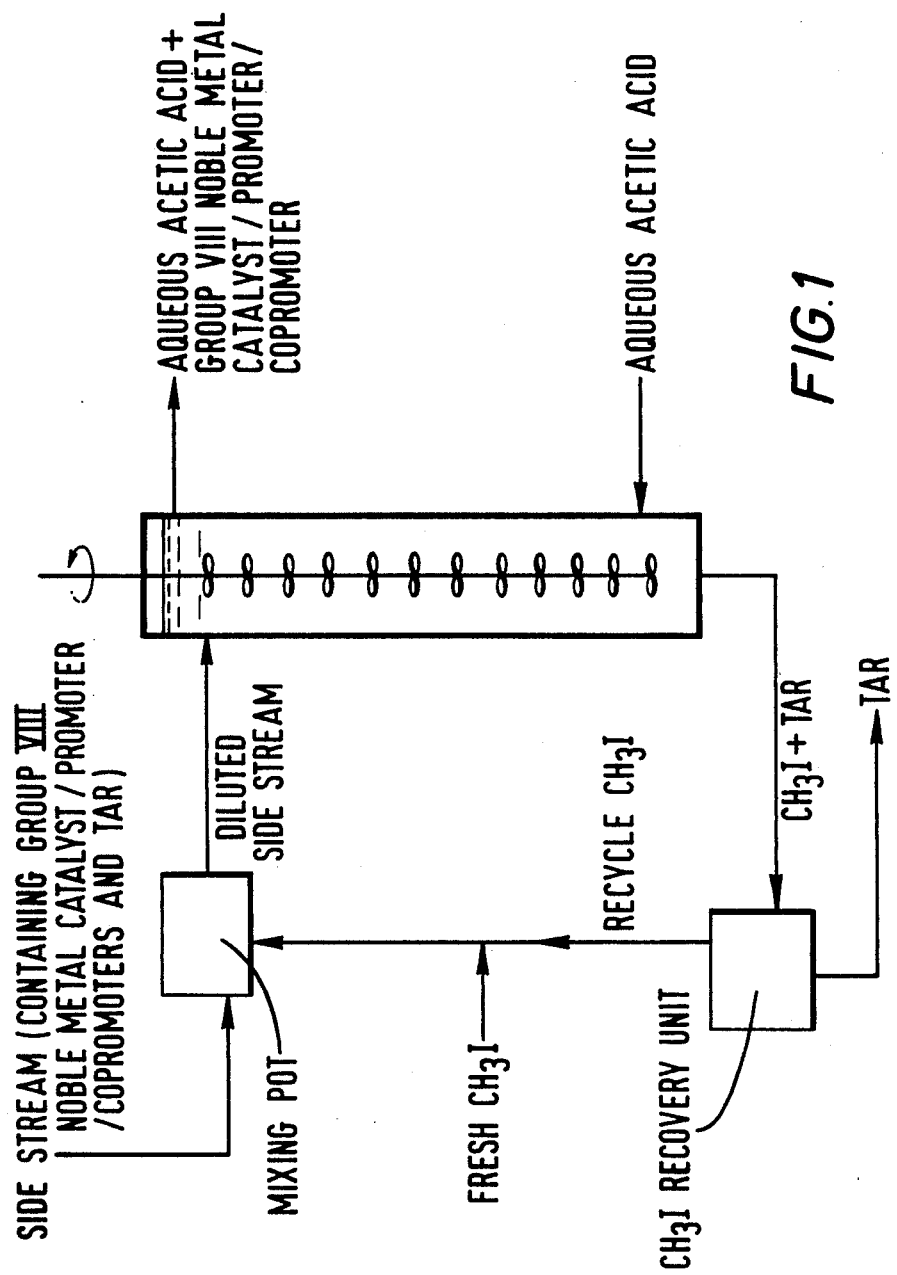
FIGS. 1 show the process of the present invention.

Accordingly the present invention provides a process for recovering a Group VIII noble metal catalyst from a process stream derived from a carbonylation process, the process stream comprising the Group VIII noble metal catalyst and methyl iodide, which process comprises contacting the process stream with an extracting stream under conditions where the Group VIII noble metal is extracted from the process stream into the extracting stream and thereafter recovering the extracting stream characterised in that the extracting stream comprises acetic acid in water.

The term Group VIII noble metal will be one which is very familiar to those skilled in the art and means any one or more of the metals ruthenium, osmium, rhodium, iridium, palladium and platinum. Preferably the Group VIII noble metal is either rhodium or iridium, more preferably rhodium.

The process stream may optionally also contain catalyst promoters and copromoters which may be recovered with the Group VIII metal. These have been discussed at length in other patents such as GB No. 1468940, 1538783, 1233121 and 1253758 and hence are likewise familiar to the skilled man. In the case of rhodium catalysts a halide promoter such as bromide or iodide along with one or more optional copromoters such as amines, phosphines, arsines, stibines and other metals (e.g. chromium, zirconium, vanadium, lithium and the like) are frequently used to achieve commercial reaction rates. Both simple and multiple catalyst/promoter/copromoter systems based on these components can be recovered using the above process.

The extracting stream preferably comprises between 30 and 90% by volume acetic acid in water. Below 30% by volume the extracting efficiency of the acetic acid falls off and becomes comparable with that achieved using water whilst at greater than 90% by volume the solubility of methyl iodide in the aqueous acetic acid becomes too high for practical purposes. However, within this range it is preferable to operate under conditions such that the ratio of methyl iodide to aqueous acetic acid is the minimum required to preserve phase separation. The extracting solution is preferably presaturated with methyl iodide before use.

The process stream, which comprises the Group VIII noble metal catalyst and any promoters and copromoters such as may be present, is suitably one which contains tar, in particular those types of tar which are generated by polymerisation of ketene or reaction of ketene with methyl acetate, acetic anhydride, ethylidene diacetate and the like. The character of such tars have been discussed in terms of their NMR spectra, infrared spectra and average empirical formula in U.S. Pat. No. 4,388,217. The process stream is preferably one which is derived by diluting a tar-containing side stream or recycle stream from the carbonylation reactor or product flash tank with methyl iodide and also optionally with water, optionally after such a stream has been concentrated to remove volatile material.

The process of the present invention is preferably operated by contacting the process stream and the extracting stream in a countercurrent manner.

After the two streams have been contacted and the Group VIII metal has been extracted the two streams are separated. The extracting stream which now contains the Group VIII metal catalyst and the optional promoters and copromoters is recycled to the carbonylation process, whilst the process stream, if it contains tar, is fed to a separation unit in which the tar and methyl iodide are separated. The methyl iodide may be recycled for further use and the tar disposed of.

The process of the present invention may be carried out, for example, as shown in FIG. 1. In this case a side stream comprising rhodium catalyst, iodide promoter, quaternary amine copromoter, tar and carbonylation reaction products is withdrawn from the carbonylation process and diluted with methyl iodide. The diluted side stream is next fed to an extraction column where it is countercurrently contacted with the acetic acid in water extracting stream. Typically this is effected by feeding the denser diluted side stream into the top of the column and removing it from the bottom and by feeding the lighter extracting stream into the bottom and removing it at the top. Good contact can be achieved by stirring or otherwise agitating the contents of the column although axial mixing should be avoided as far as possible.

The diluted side stream which is removed from the bottom of the column and which now consists of methyl iodide, tar and trace amounts of catalyst, promoter and copromoter is fed to a distillation column where the methyl iodide is recovered overhead and recycled. The tar residue is disposed of e.g. by burning.

The extracting stream removed from the top of the extraction column which now contains most of the catalyst, promoter and copromoter can now be recycled to the carbonylation reactor.

The improved efficiency of extraction which is obtained using aqueous acetic acid as the extracting stream will now be illustrated by the following Examples.

EXAMPLE 1

A side stream from a carbonylation process having the composition:

| methyl iodide | 5.3% (by weight) |
|---|---|
| methyl acetate | 6.7% |
| acetic anhydride | 17.1% |
| acetic acid | 35.4% |
| byproducts | 1.4% |
| N-methylimidazolium iodide | 29.2% |
| Tar | 4.7% |
| Rhodium catalyst | 690 ppm | was continually mixed at the rate of 1 ml/min with 3.3 ml/min of methyl iodide. The mixture was fed to an extraction column (07 QVF tubing ca 125 cm high and 1.6–1.8 cm ID), where it was countercurrently contacted at 25° C. with 10.6 ml/min of an extracting stream comprising 77% by volume acetic acid/23% by volume water.

The experiment described above was run for 3.5 hours. For the last hour, the extracting stream and tar containing mixture leaving the extraction column were separately collected and analysed. Analysis of the two by atomic absorption produced a rhodium accountability of 94% with a rhodium extraction efficiency of the extraction stream of ca 98%.

Rhodium Extraction Efficiency =

$$\frac{\text{Rh in extracting stream} \times 100}{\text{Rh in extracting stream and methyl iodide/tar stream}}$$

EXAMPLE 2

Figure 2:
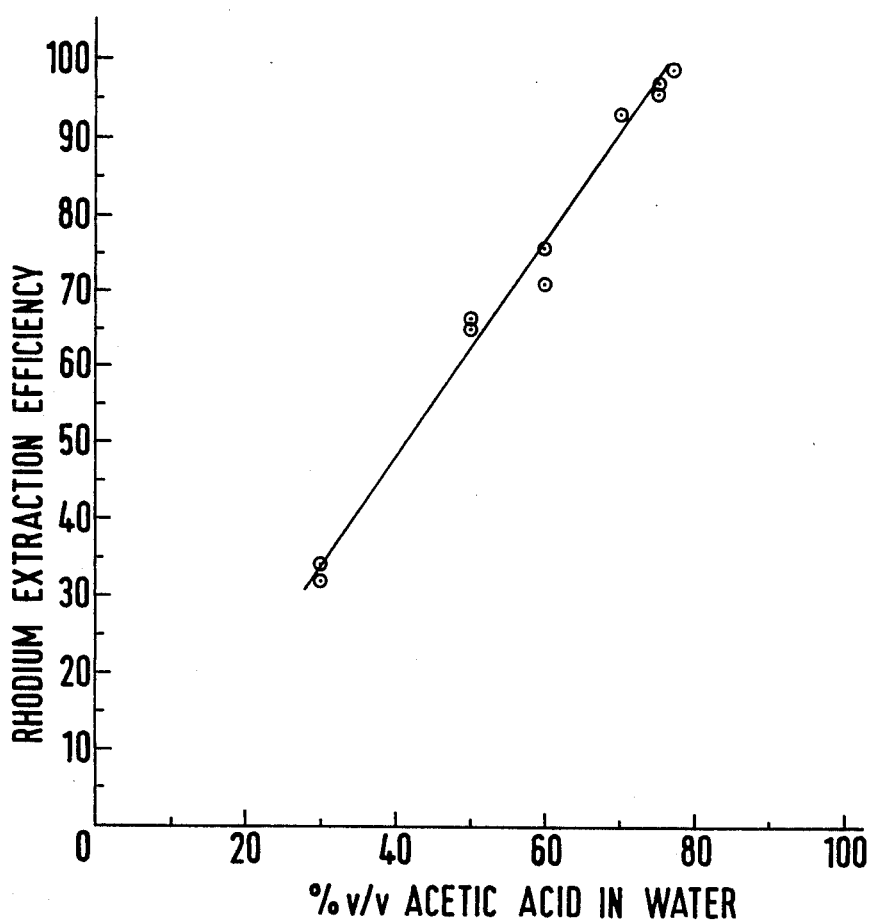
FIG. 2 shows rhodium attraction efficiency as a function of the composition of the extracting stream.

Example 1 was repeated except the volume of the extracting stream used was 5 ml/min instead of 10.6 ml/min. A series of experiments were carried out using extracting streams of differing compositions. The rhodium extraction efficiency is expressed graphically as a function of the composition of the extracting stream in FIG. 2. The results show that the rhodium extraction efficiency increases as the acetic acid content of the extracting stream increases. Rhodium accountability in these experiments were similar to that given in Example 1.

I claim:

1. A continuous process for recovering a Group VIII noble metal catalyst from tar generated by the polymerization of ketene or the reaction of ketene with one or more of methyl acetate, acetic anhydride or ethylidene diacetate, which process comprises the steps of:
   diluting the tar containing the Group VIII noble metal catalyst with methyl iodide to produce a process stream;
   thereafter contacting the diluted tar containing Group VIII noble metal catalyst with an extracting stream comprising acetic acid in water under conditions where the Group VIII noble metal is extracted from the diluted tar into the extracting stream; and
   thereafter separating the diluted tar from the extracting stream containing the Group VIII noble metal catalyst.

2. A process as claimed in claim 1, wherein the Group VIII metal is either rhodium or iridium.

3. A process as claimed in claim 1, wherein the Group VIII metal is rhodium.

4. A process as claimed in claim 1, wherein the process stream further comprises one or more promoters or copromoters selected from the group consisting of bromide promoters, iodide promoters, amine promoters, phosphine copromoters, arsine copromoters, stibine copromoters, and metal copromoters.

5. A process as claimed in claim 4, wherein said metal copromoters are selected from the group consisting of chromium, zirconium, vanadium and lithium.

6. A process as claimed in claim 1, wherein the process stream and extracting stream are contacted countercurrently.

7. A process as claimed in claim 1, which further comprises the step of recycling the extraction stream to the carbonylation process.

8. A process as claimed in claim 6, which further comprises the steps of feeding the process stream, after it has been separated from the extraction stream, to a separation unit wherein the methyl iodide and tar are separated.

9. A continuous process for recovering a rhodium or iridium catalyst from tar generated by the polymerization of ketene or the reaction of ketene with one or more of methyl acetate, acetic anhydride or ethylidene diacetate, which process comprises the step of:
diluting the tar containing the rhodium or iridium with methyl iodide to produce a process stream;
thereafter contacting the diluted tar containing the rhodium or iridium catalyst with an extracting stream comprising acetic acid in water under conditions where the rhodium or iridium is extracted from the diluted tar into the extracting stream; and
separating the diluted tar from the extracting stream containing the rhodium or iridium catalyst.

10. A process as claimed in claim 9, wherein the process stream is separated into methyl iodide for recycle and tar for disposal.

11. A process as claimed in claim 1, wherein there is used 30 to 90% by volume acetic acid in water.

12. A process as claimed in claim 1, which is carried out at a temperature of less than the boiling point of methyl iodide under the conditions of the process.

* * * * *